United States Patent [19]

Dessau

[11] 4,384,153

[45] May 17, 1983

[54] DIELS-ALDER CYCLIZATION OVER LOW ACIDITY LARGE-PORE ZEOLITES

[75] Inventor: Ralph M. Dessau, Edison, N.J.

[73] Assignee: Mobil Oil Corporation, New York, N.Y.

[21] Appl. No.: 359,397

[22] Filed: Mar. 18, 1982

[51] Int. Cl.$^3$ .............................................. C07C 3/035
[52] U.S. Cl. .................................... 585/366; 585/361; 585/365; 585/367
[58] Field of Search ............... 585/361, 362, 365, 366, 585/367, 368, 369

[56] References Cited

U.S. PATENT DOCUMENTS 3,444,253  5/1969  Reimlinger et al. ................ 585/366

FOREIGN PATENT DOCUMENTS 1138126  12/1968  United Kingdom ................ 585/366

OTHER PUBLICATIONS

Reimlinger et al., Chem. Ber., 103 (7), 2317 (1970).

*Primary Examiner*—Delbert E. Gantz
*Assistant Examiner*—A. Pal
*Attorney, Agent, or Firm*—Charles A. Huggett; Michael G. Gilman; Charles J. Speciale

[57] ABSTRACT

The present invention provides a process which is adapted for cyclodimerization of 1,3-butadiene to 4-vinylcyclohexene-1 under Diels-Alder conditions in the presence of a low acidity form of a large-pore zeolite such as ZSM-20, beta or Y.

4 Claims, No Drawings

DIELS-ALDER CYCLIZATION OVER LOW ACIDITY LARGE-PORE ZEOLITES

BACKGROUND OF THE INVENTION

This invention relates to a catalytic process for the cyclization of alkene compounds, as exemplified by the cyclodimerization of 1,3-butadiene to 4-vinylcyclohexene-1 utilizing as a catalyst a low acidity form of a large-pore zeolite such as ZSM-20, beta or Y.

DESCRIPTION OF THE PRIOR ART

U.S. Pat. No. 3,444,253 discloses and claims a process for the dimerization of 1,3-butadiene to produce 4-vinylcyclohexene-1 using copper(I) zeolite X, or copper(I) zeolite Y. The present invention represents an effective alternative to the process of said patent in that it has been found that a high Diels-Alder conversion can be obtained by utilizing zeolite ZSM-20 and/or zeolite beta and/or zeolite Y in their low acidity form, without the need for a copper(I) metal component.

DESCRIPTION OF THE PREFERRED EMBODIMENTS

It is to be noted that the large-pore crystalline aluminosilicates with which this invention is concerned are well known in the art. Zeolite ZSM-20 is disclosed and claimed in U.S. Pat. No. 3,972,983, zeolite beta is disclosed and claimed in U.S. Pat. No. Re. 28,341, and zeolite Y is disclosed and claimed in U.S. Pat. No. 3,130,007.

An essential aspect of the present invention process involves the use of a low acidity form of a large-pore zeolite catalyst such as ZSM-20 and beta or Y zeolites, i.e., usually the alkali metal form and, more preferably, the sodium form in order to reduce their acid activity to an insignificant level. Other ways of reducing the acid activity other than by alkali metal exchange include steaming the zeolite, or other means of aluminum removal.

The low acid activity of zeolite catalysts is conveniently defined by the Alpha scale described in an article published in the Journal of Catalysis, Vol. VI, pp. 278-287 (1966). In general, the zeolites according to this invention have low Alpha values (less than about 10), and preferably the Alpha value is substantially lower than unity. As noted, the low acid activity may be achieved by using a severe high temperature steaming means of de-aluminizing zeolites and/or ion-exchange in any combination. For example, zeolites having a silica-to-alumina ratio of about 40 may be treated with 100% steam at 1200° F. for a period of time (several hours) adequate to reduce the acid activity to the necessary level.

However, as has been indicated earlier, the most preferred method of obtaining the low acidity is achieved by extensive ion-exchange of the zeolite with sodium or other alkali metal cations. Silica-to-alumina ratios in the range of 12 to infinity will generally characterize the zeolites preferred in the form of the invention.

The alkali metal content (e.g., sodium) of the zeolites will vary inversely with the silica-to-alumina ratio since it is the aluminum atoms which provide cationic sites suitable for acceptance of alkali metal cations. Depending on that ratio, sodium content may vary up to about 10 weight percent of the metal. Content of other alkali metals will vary from those numbers on a weight basis in proportion to atomic weights.

By the term "large-pore" as employed herein with reference to zeolites is meant a crystalline zeolitic substrate which has a constraint index less than about 2.0, when measured in its hydrogen form.

A simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons.

As has heretofore been stated, the novel process of this invention is adapted for cyclodimerization of 1,3-butadiene, in the presence of a low acidity ZSM-20 and/or beta and/or Y type of zeolite catalyst as previously described. The cyclodimerization of 1,3-butadiene proceeds as follows to yield 4-vinylcyclohexene-1:

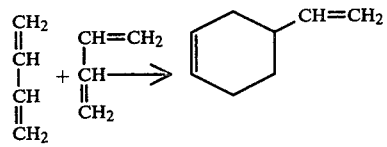

Other alkadienes which can be cyclodimerized are illustrated by isoprene, chloroprene, 1,3-pentadiene, cyclopentadiene, and the like. The cyclodimerization also can be effected between different conjugated dienes, and between dienes and monoalkenes, and the like. For example, maleic anhydride can be reacted with cyclopentadiene. Conjugated alkadienes can also be co-cyclized with alkynes such as dimethylacetylene.

An important advantage of the invention process is that high conversions are obtained with copper-free zeolites as opposed to the prior art methods of carrying out said reaction in the manner previously described. The invention process can be conducted in several ways, including continuous process in the gas phase or in the liquid phase, or as a batch process. The 1,3-butadiene dimerization, for example, can be accomplished at temperatures in the range of about room temperature to temperatures as high as 400° C. or 500° C. However, the preferred temperature range is about 150° C. to 300° C. The reaction preferably is conducted at a pressure of about 50–1000 psi, and the product is recovered from the reaction mixture by standard procedures such as fractional distillation or the like.

It was unexpected that a Diels-Alder reaction such as the cyclodimerization of 1,3-butadiene to 4-vinylcyclohexene-1 could be significantly catalyzed by zeolites without the necessity of adding copper in the plus one valence state as has heretofore been the case with prior art zeolites (e.g., as described in U.S. Pat. No. 3,444,253).

It is an important aspect of the invention process that the cyclization product resulting from the catalyzed Diels-Alder reaction must have sufficiently small molecular dimensions to permit the diffusion of the said product out of the large-pore structure of the low acidity zeolite catalyst.

The following examples are further illustrative of the invention process.

EXAMPLES 1–6

The cyclodimerization of 1,3-butadiene was conducted in a downflow glass reactor packed with 5–10 gms. of catalyst. The 1,3-butadiene flow was adjusted to about 10 cm/min. and the temperature raised to about 200° to 250° C. The reaction effluent was sampled with an in-line gas chromatograph and the liquid product was collected for analysis by gas chromatograph mass spectroscopy. The results obtained were as follows:

| Catalysis Of 1,3-Butadiene Cyclodimerization | | | |
|---|---|---|---|
| Example | Catalyst | % Conversion | C.I. (of H form) |
| 1 | None | 0.1 | |

-continued

| Catalysis Of 1,3-Butadiene Cyclodimerization | | | |
|---|---|---|---|
| Example | Catalyst | % Conversion | C.I. (of H form) |
| 2 | Na—ZSM-20 | 20 | 0.6 |
| 3 | Na—beta | 10 | 0.6 |
| 4 | Na—Y | 4 | 0.6 |
| 5 | Na—ZSM-12 | 0.5 | 2 |
| 6 | Na—ZSM-5 | 0.2 | 8 |

The above table illustrates the novel process of this invention in that the sodium form of zeolite ZSM-20 and zeolite beta in Examples 2 and 3 unexpectedly resulted in exceptional conversions of 1,3-butadiene to 4-vinylcyclohexene-1, and Na-Y zeolite in Example 4 provided a significant conversion of 1,3-butadiene to the desired product.

The Examples 5–6 results indicated that Na-ZSM-12 and Na-ZSM-5 zeolites exhibited low reactivity as Diels-Alder cyclization catalysts.

What is claimed is:

1. A process for cyclodimerization of a conjugated alkadiene which comprises contacting a conjugated alkadiene-containing feedstock with ZSM-20 zeolite catalyst having an Alpha value less than about 1.0, at a temperature between about 150°–300° C. to yield cyclodimerized product.

2. A process in accordance with claim 1 wherein the conjugated alkadiene is 1,3-butadiene, and the cyclodimerized product is 4-vinylcyclohexene-1.

3. A process for cyclodimerization of a conjugated alkadiene which comprises contacting a conjugated alkadiene-containing feedstock with beta zeolite catalyst having an Alpha value less than about 1.0, at a temperature between about 150°–300° C. to yield cyclodimerized product.

4. A process in accordance with claim 3 wherein the conjugated alkadiene is 1,3-butadiene, and the cyclodimerized product is 4-vinylcyclohexene-1.

* * * * *